United States Patent [19]

Pennington

[11] Patent Number: 4,883,889
[45] Date of Patent: * Nov. 28, 1989

[54] ALKYLENE OXIDES PRODUCTION USING MOLTEN NITRATE SALT CATALYST AND A CO-CATALYST

[75] Inventor: B. Timothy Pennington, Sulphur, La.

[73] Assignee: Olin Corporation, Cheshire, Conn.

[*] Notice: The portion of the term of this patent subsequent to Nov. 15, 2005 has been disclaimed.

[21] Appl. No.: 182,617

[22] Filed: Apr. 18, 1988

Related U.S. Application Data

[63] Continuation-in-part of Ser. No. 929,552, Nov. 12, 1986, Pat. No. 4,785,123.

[51] Int. Cl.$^4$ .............................................. C07 301/06
[52] U.S. Cl. .................................... 549/532; 549/533
[58] Field of Search ................................ 549/532, 533

[56] References Cited

U.S. PATENT DOCUMENTS

| | | | |
|---|---|---|---|
| 2,366,724 | 1/1945 | Gardner | 260/348 |
| 2,530,215 | 11/1950 | Cook | 260/348.5 |
| 3,132,156 | 5/1964 | Lemon et al. | 260/348 |
| 3,641,157 | 2/1972 | Riegel et al. | 260/348 |
| 3,647,358 | 3/1972 | Greenberg | 549/533 |
| 3,786,109 | 1/1974 | Jones | 549/533 |
| 3,850,742 | 11/1974 | Dugan et al. | 208/114 |
| 4,785,123 | 11/1988 | Pennington | 549/532 |

FOREIGN PATENT DOCUMENTS 968364 5/1975 Canada .

Primary Examiner—Glennon H. Hollrah
Assistant Examiner—Ba Trinh
Attorney, Agent, or Firm—Dale Lynn Carlson

[57] ABSTRACT

A process for producing an alkylene oxide or mixture of alkylene oxides by a reaction which comprises reacting an olefin or mixture thereof with an oxygen-containing gas in the presence of at least one molten nitrate salt and a co-catalyst.

17 Claims, No Drawings

ALKYLENE OXIDES PRODUCTION USING MOLTEN NITRATE SALT CATALYST AND A CO-CATALYST

This is a continuation-in-part application of U.S. patent application Ser. No. 929,552, filed Nov. 12, 1986, now U.S. Pat. No. 4,785,123.

BACKGROUND OF THE INVENTION

Alkylene oxides (vicinal epoxy alkanes), and particularly propylene oxide, are very valuable and widely used chemicals. They have been polymerized with a useful in coating compositions and in the manufacture of molded articles. Alkylene oxides have also been reacted with alcohols to yield monoalkyl ethers which have utility as solvents in many commercial processes and which are useful as components for synthetic turboprop and turbojet lubricants.

There are many methods known in the art for the production of alkylene oxides and, most notably, propylene oxide. One of the oldest methods is the so-called "chlorohydrin process" which involves the reaction of chlorine and water to form hypochlorous acid which is then reacted with propylene to form propylene chlorohydrin. The propylene chlorohydrin is then dehydrohalogenated to yield propylene oxide. Another method to obtain propylene oxide is by the liquid phase oxidation of propylene with organic peracids. Still another method involves the liquid phase oxidation of propylene with t-butyl hydroperoxide and/or ethylbenzene hydroperoxide.

The aforementioned known methods have serious disadvantages associated therewith. For example, the "chlorohydrin process" requires the use of chlorine which is relatively expensive and corrosive in nature, requiring special handling and expensive equipment. Additionally, the chlorohydrin saponification to propylene oxide consumes alkali chemicals such as caustic soda or lime, producing a large aqueous waste stream containing chloride salts, which require costly treatment prior to discharge from the plant. The oxidation of propylene with peracids is a potentially dangerous operation and expensive equipment is needed to guard against potentially explosive hazards when working with the peracids. Another disadvantage of this method is the high cost of peracids. The t-butyl hydroperoxide and ethylbenzene hydroperoxide processes have the disadvantages of being capital-intensive, multi-step, rather complicated processes. Furthermore, these processes require co-feedstocks of isobutane or ethylbenzene, thus constraining the practical utility of the processes for propylene oxide manufacture.

Another method which has received considerable attention in the literature is the direct oxidation of hydrocarbons with an oxygen-containing gas. This method suffers from the disadvantage that it is not specific for the production of alkylene oxides but produces a variety of other compounds including acids, esters, ethers, and oxides of carbon including carbon monoxide and carbon dioxide. The reaction does, however, possess two attributes which recommend it highly for commercial utilization, i.e., inexpensiveness of starting materials and simplicity of operation. It is primarily for these reasons that much attention in recent years has been directed to improvements in methods for the production of alkylene oxides from the direct oxidation of hydrocarbons even though the producer must necessarily contend with the concurrent production of a variety of undesired products.

By way of illustration, the prior art methods which attempted to produce propylene oxide by the oxidation of propane such as that disclosed in U.S. Pat. No. 2,530,509, assigned to Linde Air Products Company, were only partially successful. The majority of the prior art methods used conventional vertical columns and differed from each other by variations in lengths and diameter of the column, temperature, pressure, etc. However, all of these methods suffered one common disadvantage--the temperature of the reactants varied throughout the length of the column.

The temperature variations are easily explained since the oxidation reactions are exothermic and the amount of heat evolved differs with each reaction which is taking place. Thus, at various increments along the tube, conditions existed which favored the direction of the oxidation to products other than propylene oxide. These prior art methods necessitated the use of elaborate and expensive cooling apparatus.

Further developments in the art constituted attempts to maximize the desired olefin oxide production while minimizing by-product formation. For example, U.S. Pat. No. 3,132,156, assigned to Union Carbide Corporation, discloses the vapor phase oxidation of saturated aliphatic hydrocarbons to olefin oxides. The method described in this '156 patent is said to provide enhanced olefin oxide production as high as 46.2 lbs per 100 lbs of $C_3$ consumed which calculates to be about 33 percent (molar) selectivity. While this level of selectivity constituted an improvement, it remains less than might be desired from a commercial standpoint. Likewise, Canadian Pat. No. 968,364, assigned to Union Carbide Corporation, discloses the indirect oxidation of olefin oxides via the oxidation of methanol to a free radical intermediate which in turn, epoxidizes the olefin. However, the indirect oxidation method disclosed in the Canadian '364 patent has the disadvantage of requiring the use of a solvent together with subsequent solvent separation step(s). Accordingly, new methods of producing olefin oxides that combine enhanced selectivity with a simple, inexpensive process would be highly desirable.

SUMMARY OF THE INVENTION

The present invention relates to a process for producing an alkylene oxide or mixture of alkylene oxides by a reaction which comprises reacting an olefin having from 3 to 22 carbon atoms per molecule, or mixture thereof, with an oxygen-containing gas, said olefin and said oxygen-containing gas being gaseous reactants, by contacting said gaseous reactants with a bath, stream, spray or mist of at least one molten nitrate salt catalyst and a co-catalyst, said catalyst being present in an amount sufficient to absorb any heat generated during said reaction while maintaining an essentially constant reaction temperature, said co-catalyst being an elemental metal, or oxide or hydroxide thereof, which is suspended, dispersed or dissolved in said catalyst, said reaction being conducted at a reaction temperature of between about 135° C. and about 600° C. and a reaction pressure of between about 1 and about 50 atmospheres.

DETAILED DESCRIPTION OF INVENTION

Several factors will affect the reactant conversion to alkylene oxide and the selectivity of alkylene oxide production vis-a-vis by-product production in accordance with the process of the present invention. These factors include, for example: the contact time of the molten salt with the oxygen-containing gas, the temperature of the reactor product gases, the molten salt temperature, the molten salt catalyst composition, the feed gas temperature, the feed gas composition, the feed gas pressure, and the co-catalyst employed.

The oxygen-containing gas useful as a reactant in the present invention can be any such gas. Typically, air is employed as the oxygen-containing gas based upon its ready availability. However, other oxygen-containing gases such as pure oxygen may be employed if desired, and the use of oxygen is expected to be preferred in a commercial setting.

The olefin useful in the present invention can be broadly defined as an epoxidizable, olefinicallyunsaturated hydrocarbon compound having from 3 to 22 carbon atoms, preferably from 3 to 15 carbon atoms, more preferably from 3 to 12 carbon atoms, most preferably from 3 to 8 carbon atoms. This definition is intended to include terminal olefins selected from the group consisting of monofunctional and difunctional olefins having the following structural formulas respectively:

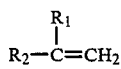

wherein $R_1$ is hydrogen or an alkyl chain, straight or branched, having 1 to 20 carbon atoms and $R_2$ is an alkyl chain, straight or branched, having 1 to 20 carbon atoms; and

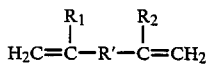

wherein $R_1$ and $R_2$ are hydrogen atoms or alkyl chains having 1 to 10 carbon atoms and $R'$ is from 2 to 10 methylene groups. The definition also includes cyclic olefins and internal olefins. The ring portions of the cyclic olefins can have up to 10 carbon atoms and one unsaturated bond and can be substituted with one or two alkyl radicals having 1 to 10 carbon atoms. The cyclic olefins are typically represented by the following structural formula:

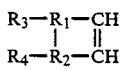

wherein $R_1$ and $R_2$ are olefin radicals having 1 to 4 carbon atoms and $R_3$ and $R_4$ represent hydrogen atoms, or one or two alkyl radicals, straight or branched chain, having 1 to 10 carbon atoms. The internal olefins are represented by the following structural formula:

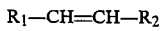

wherein $R_1$ and $R_2$ are straight chain or branched chain alkyl radicals having 1 to 10 carbon atoms.

The olefins, and mixtures thereof, useful as reactants in accordance with the present invention generally have up to, but do not exceed, about 22 carbon atoms per molecule, preferably not more than 12 carbon atoms per molecule. When a straight-chain molecule is employed, it is more preferred that such molecule not have more than five carbon atoms. When a cyclic compound is used, it is more preferred that the cyclic compound not have more than 12 carbon atoms per molecule. Illustrative reactants include, propylene, isobutylene, cyclohexene, and mixtures thereof. A preferred reactant within this group is propylene or a mixture of propylene and propane based upon their commercial availability.

Representative other olefins are butene-1, butene-2, pentene-1, hexene-1, pentene-2, cyclopentene, and cyclooctene. Other representative olefins are 2-methylbutene-1, 3-methylbutene-1, heptene-1, octene-1, hexene-2, hexene-3, octene-2, heptene-3, pentadecene-1, octadecene-1, dodecene-2, 2-methylpentene-2, tetramethylethylene, methylethylethylene, cyclobutene, cycloheptene, 2-methylheptene-1, 2,4,4-trimethylpentene-1, 2-methyl- butene-2, 4-methylpentene-2, 2-ethyl-3-methylbutene-1, and styrene.

The olefin gas is preferably preheated to prevent condensation in the line delivering this gas to the reactor. Alternatively, both the oxygen-containing gas and the olefin gas (collectively referred to herein as "the feed gases") can be preheated to prevent condensation in any of the feed lines. However, in the absence of preheat, the molten nitrate salt will rapidly heat the feed gases up to reaction temperature. If the feed gas is preheated, it preferably is maintained at at least about 100° C. in the feed gas line(s).

The molten nitrate salt(s) catalyst is generally maintained at a temperature sufficient to keep the salt(s) in a molten condition. Preferably, the temperature is maintained between about 135° C. (275° F.) and about 600° C. (1,000° F.), more preferably between about 200° C. and about 600° C., most preferably between about 250° C. and about 550° C. during the reaction in accordance with the present invention.

The specific temperature selected is based upon the melting point of the particular molten nitrate salt chosen. For example, mixtures of molten lithium and potassium nitrate can be suitably employed at a temperature as low as about 280° F., and hence, this temperature may be employed when using lithium nitrate. In the selection of a suitable molten salt bath temperature, it is important to choose a temperature below the thermal decomposition temperature for the particular molten nitrate salt chosen. In addition, it is important to maintain a sufficient isotherm across the molten nitrate salt bath so as to avoid crust formation of the nitrate salt in the bath. Such a crust formation in the nitrate salt bath can cause localized overheating of gases trapped by the crust in the bath and an associated "runaway" oxidation reaction due to overheating of the gases in the bath. In order to maintain a bath isotherm, constant stirring of the molten nitrate salt bath is preferred. Alternatively, the molten salt can be circulated by conventional means, such as the use of internal draft tubes or external pumping loops.

The nitrate salt catalyst used may be any one of the alkali or alkaline earth nitrates such as lithium, sodium, potassium, rubidium, cesium, magnesium, calcium, strontium, or barium or mixtures thereof. In addition, the nitrate salts can be used in mixtures with other salts such as chlorides, bromides, carbonates, sulfates, and phosphates. Generally, the content of the other salt(s), when present, should be restricted to less than 60 percent by weight based upon the weight of the total melt and in most cases their contents should not exceed about 25 percent of the total melt.

The ratio of olefin to oxygen in the oxygen-containing gas in the reactor can vary over a wide range. However, in accordance with the present invention, it has now been found that enhanced selectivity of alkylene oxide product is achieved by maintaining a relatively low amount of oxygen relative to the amount of olefin fed into the reactor. For example, when reacting propylene with oxygen in a molten potassium nitrate salt column at atmospheric pressure, a ratio of between about 1 and about 20 volume percent of oxygen, e.g., about 5 volume percent oxygen to about 95 volume percent propylene has been found to provide an enhanced selectivity of propylene oxide. When using air as the oxygen-containing gas, it is preferably employed in an amount of between about 5 and about 75 volume percent based upon the total amount of air plus propylene employed in the reaction. Another consideration in the selection of the amount of propylene or other olefin to use as a feed is the high partial pressure of the olefin which in high concentrations can cause thermal cracking of the olefin reactant itself. Therefore, when conducting the oxidation reaction at an elevated pressure, viz 75 psig, it is preferred to "cut" the amount of propylene in the illustrative example to 75 volume percent and utilize an inert blanket ("diluent") gas, such as nitrogen, to provide the remaining 20 volume percent of feed gas. Alternatively, the diluent gas may be comprised of mixtures of oxidation by-product gases such as acetaldehyde, methane, and carbon dioxide, generally readily obtainable from the propylene oxide purification operations downstream of the molten salt reactor.

In the selection of the ratio of the volume of oxygen-containing gas relative to the volume of olefin employed in the reaction mixture, the range of ratios which might pose a flammability hazard should be avoided, as is well known. For example, when utilizing an air/propylene reactant mixture at atmospheric pressure, the range of below 12 volume percent of propylene based upon total air plus propylene should be avoided.

In accordance with the present invention, it has been found that when an elemental metal, or the oxide or hydroxide thereof, when employed as a co-catalyst in conjunction with the molten nitrate salt catalyst, makes it possible to lower the reaction temperature for the particular nitrate salt selected and/or enhance the selectivity or conversion to the desired olefin oxide. For example, it has been found in accordance with the present invention that although a temperature of about 380° C. is normally required when reacting propylene with air to produce propylene oxide in the presence of sodium nitrate at atmospheric pressure, the temperature can be reduced to 350° C. provided that a co-catalyst of palladium on alumina is employed in conjunction with the molten salt. A silver co-catalyst such as silver nitrate is expected to similarly reduce the required reaction temperatures. The use of these metal co-catalysts are preferred when the reaction is conducted at atmospheric pressure. At superatmospheric pressure, an alkali metal hydroxide co-catalyst, such as sodium hydroxide, has been found to be particularly advantageous in providing enhanced selectivity to the desired product. In addition, in a continuous process employing caustic recycle, the alkali metal hydroxide is expected to enhance the desired product distribution by removing by-product carbon dioxide by forming alkali metal carbonate.

The co-catalyst is generally employed in a catalytically effective amount, generally in an amount of less than about 5 (preferably between about 0.5 and about 5, more preferably in an amount between about 0.5 and about 3) weight percent based on the total amount of co-catalyst plus molten salt catalyst.

The molten salt catalyst in which the co-catalyst is suspended or dispersed, helps to maintain the co-catalyst at a constant desired temperature or isotherm. The maintenance of the co-catalyst in such an isotherm makes it possible to reduce or avoid the problems of co-catalyst de-activation that might otherwise be encountered in a non-isothermal system due to overheating of the co-catalyst itself or due to thermal degradation of product to a tarry by-product which can coat, and thus de-activate, the catalyst.

The molten salt(s), in addition to functioning as a catalyst and as an isothermal medium for the co-catalyst, also serve as a temperature regulator. More specifically, the molten nitrate salt(s) have a high heat absorption capacity enabling them to absorb large quantities of heat during the exothermic oxidation reaction while maintaining an essentially constant reaction temperature and thereby preventing a runaway reaction. The absorbed heat of reaction from this exothermic oxidation may be employed in the process of the present invention to help maintain the molten salt in a molten state and/or to heat the gaseous reactants to reaction temperature.

In a preferred embodiment of the present invention, a mixture of potassium and sodium molten nitrate salts is employed comprising between about 20 and about 80 weight percent of sodium nitrate, preferably between about 45 and about 65 weight percent of sodium nitrate based upon the total amount of sodium nitrate and potassium nitrate in the molten salt mixture.

One method of contacting the gaseous reactants in the presence of the molten nitrate salt is by bubbling the reactants through a bath of the molten salt. If the gaseous reactants are bubbled into the bottom of the bath or column containing the molten nitrate salt, the contact time of the reactants with the molten salt catalyst is equal to the "rise time" of the reactants through the bath or column. Thus, the contact time can be increased by increasing the length of the molten nitrate salt bath or column. An alternate method of contacting the gaseous reactants in the presence of the molten salt would be to pass the gaseous reactants through a reactor countercurrently to a spray or mist of the molten salt. This latter method provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. This latter method is expected to be preferred in a commercial setting. These methods are only illustrative of types of reaction systems which may be employed in the practice of this disclosure. Other conventional methods of gasliquid contact in reaction systems may also be employed.

The olefin feed gas(es) can be passed into the molten nitrate salt-containing reactor using a separate stream (e.g. feed tube) from the stream delivering the oxygen-containing gas to the reactor. Alternatively, the reactant gases can be fed into the reactor together in a single stream. In a preferred embodiment of the present invention, two co-axially-mounted feed gas tubes are employed. The co-axial mounting of the feed gas tubes has been found to reduce or minimize the back-up of molten salt into an unpressurized feed tube if pressure is temporarily lost in either (but not both) feed tube. Mixing of the gaseous reactants prior to, or at the point of, the gas(es) inlet into the reactor is desired in order to facilitate the oxidation reaction. Mixing is suitably accomplished using an impingement mixer or sparger tube.

The feed gas is preferably bubbled into the molten nitrate salt-containing reactor using a sparger. If used, the sparger is preferably positioned in the molten nitrate salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube. The feed gas tubes are preferably co-axially mounted so that in the event of a loss of pressure in either gas tube, the gas in the other tube will maintain sufficient pressure to keep the molten salt from backing up into the unpressurized feed gas tube.

This process can be run in a batchwise or continuous operation, the latter being preferred. The order of introduction of the reactants is determined by the operator based on what is most safe and practical under prevalent conditions. Generally, the desirability of avoiding flammable gas mixtures throughout the reaction and subsequent product separation systems will dictate the desired procedures.

The process can be carried out by feeding a mixture of olefin, inert gas, and oxygen into a reaction vessel containing molten nitrate salt. The reaction vessel can be glass, glass-lined metal, or made of titanium. For example, a glass-lined stainless steel autoclave can be used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten salt(s)/feed gas mixture is preferred to avoid a static system and insure the homogeneity of the molten salt, agitation helps prevent crust formation of the salt(s) at the head gas/salt interface in the reactor. This can be accomplished by using a mechanically stirred autoclave, a multi-point injection system, or a continuous process, e.g., with a loop reactor wherein the reactants are force circulated through the system. Sparging can also be used. In the subject process, it is found that increased rates of reaction are obtained by good gas-liquid contact provided by agitation of the molten salt/gas mixture.

The process of the present invention is suitably carried out at atmospheric, subatmospheric or superatmospheric pressure. Typically, the process is effected at superatmospheric pressures of up to about 100 atmospheres, preferably between about 1 atmosphere and about 50 atmospheres, more preferably between about 1 atmosphere and about 35 atmospheres. The most preferred pressure range is between about 1 and about 25 atmospheres.

It is to be understood that by-products are also produced during the reaction. For example, some fragmentation and dehydrogenation of the propylene feed is also effected, particularly at higher temperatures within the hereinabove noted temperature range, and therefore, the reaction conditions are generally controlled to minimize such production. The separation of the resulting by-products in order to recover the desired product may be effected by a wide variety of well-known procedures such as: absorption in water followed by fractional distillation, absorption, and condensation.

The following examples are intended to illustrate, but in not way limit the scope of, the present invention.

EXAMPLE 1

Sodium Hydroxide Co-Catalysis of a Vapor Phase Oxidation of Propylene With Air at Elevated Pressures (75 psig)

A salt mixture consisting of 1320 g sodium nitrate, 880 g potassium nitrate, and 50 g sodium hydroxide was added to a two-liter stainless steel autoclave with a Hastelloy C liner. The salt mixture was melted and brought up to 350° C. by means of an external electrical resistance heater. Propylene and air, each at a rate of 1000 cc/min, were sparged into the melt through separate but concentric co-axial tubes with a sparging element attached to the end. The sparging element forced the two feed gases to mix just before entering the molten salt. The feed gases were sparged into the melt and allowed to exit the melt and the reactor in a continuous manner. The reactor pressure was brought up to 75 psig, and the reactor temperature was brought up to 380° C. while maintaining a continuous flow through reactor condition. After holding the reaction conditions constant for one hour, the exit gases and the liquid condensed in an ice water trap were analyzed. The trap was found to be empty. The reaction off gas was analyzed by three different gas chromatography methods and found to contain mainly propylene oxide and acetaldehyde. The carbonate content of the salt was also analyzed to determine how much carbon dioxide was produced. The propylene conversion was calculated to be 12.5 percent. The selectivity to propylene oxide (on a molar basis) was found to be 46 percent. The other selectivities were: acetaldehyde, 12 percent; carbon dioxide, 28 percent; and formaldehyde, 4 percent, with lessor amounts of about 10 different compounds.

COMPARATIVE EXAMPLE A

Vapor Phase Oxidation of Propylene With Air at Elevated Pressures (75 psig) Without Co-Catalyst A 250 ml gas sample cylinder fitted with a ¼ inch gas feed line at one end and a ¼ inch exit line at the other end was immersed into a molten nitrate salt bath as described in EXAMPLE 1 (but without sodium hydroxide) at 360° C. Propylene at a feed rate of 1000 cc/min and air at a feed rate of 1000 cc/min were mixed and passed through the 250 ml cylinder immersed in molten salt. The system was maintained at 75 psig by use of a backpressure regulator. The gas exiting the backpressure regulator passed through an ice water trap for condensible substances and through a gas sample cylinder in line after the trap. After a one hour reaction time, the trap was found to contain 14.5 ml of liquid which subsequent analysis showed to be about 80 percent water. The pH of the liquid was found to be about 3.0 which indicated the presence of organic acids such as formic acid and acetic acid. The water soluble organics consisted mainly of methanol, formaldehyde, allyl alcohol, acetaldehyde, propylene oxide, acetone, and traces of organic acids. The reactor exit gases were analyzed by gas chromatography and found to contain propylene oxide, acetaldehyde, ethylene, ethane, methane, methanol, formaldehyde, along with carbon dioxide and large amounts of carbon monoxide as the major products. The conversion of propylene was calculated to be 12.6 percent. The selectivity to propylene oxide was found to be 20 percent. The other selectivities were: acetaldehyde, 15 percent; carbon dioxide, 13 percent; carbon monoxide, 15 percent; formaldehyde, 5 percent; ethylene, ethane, and methane, 8 percent combined; with about 10 other compounds comprising the remainder.

A comparison of the results of this comparative example to the results given in EXAMPLE 1 shows that the vapor phase oxidation provided about the same or slightly better conversion of propylene (12.6 percent versus 12.5 percent) but poorer selectivity (20 percent propylene oxide selectivity versus 46 percent) as compared to the molten nitrate salt catalyzed oxidation of EXAMPLE 1. Enhanced selectivity is considered to be the most important of these two parameters.

PROPOSED EXAMPLE

Carbon Dioxide Removal Benefit Provided by Recycle of Caustic

After using the molten nitrate salt mixture in EXAMPLE 1 until all of the hydroxide ions had been converted into carbonate ions by reaction with carbon dioxide, 100 g of the molten salt is filtered to remove the insoluble portion of the sodium and potassium carbonates. Filtration is accomplished using heated stainless steel Buchner funnels with a porous metal frit as the filtering element and vacuum to pull the molten salt through the frit quickly. A total of 4.5 grams of solid to be a mixture of sodium and potassium carbonates (about 90 percent) and sodium and potassium nitrate (about 10 percent). This solid is heated in a muffle furnace at 1000° C. for six hours to give 2.4 grams of a mixture of sodium and potassium oxide. The bulk of the gases escaping the furnace is composed of carbon dioxide. The solid sodium and potassium oxide is exposed to humid carbon dioxide free air to convert it to sodium and potassium hydroxide. The solid sodium and potassium hydroxide is added to 100 g of a fresh melt of sodium and potassium nitrate to re-establish about a one percent level of hydroxide ion in the melt.

EXAMPLE 2

Palladium on Alumina Co-Catalyzation With Molten Nitrate Salt ($NaNO_3$/$KNO_3$) Mixture at Atmospheric Pressure In order to determine the efficacy of palladium on alumina as a co-catalyst in a molten nitrate salt bath at atmospheric pressure, the following test was conducted.

For purposes of this test, two gas compositions were employed, Gas Composition 1 containing 75 percent air and 25 percent propylene and added to the reactor at a flow rate of 1000 cc per minute; and Gas Composition 2 containing 12 percent pure oxygen and 88 percent propylene and added to the reactor at a flow rate of 850 cc per minute.

To a reactor analogous to that described in EXAMPLE 1 was charged a molten salt mixture as described in EXAMPLE 1. Either Feed Gas 1 or Feed Gas 2 was added to the reactor, as more fully identified in TABLE I below. The molten salt temperature was maintained at either 350° C. or 400° C., as identified in TABLE I below. Sparging of the selected gas composition into the reactor was made at the above-identified flow rates and conducted for 30 minutes with product and by-product gases exiting the reactor at atmospheric pressure. The product gases were analyzed for conversions and molar selectivity. These are identified in TABLE I below.

TABLE I

Comparison of Atmospheric Pressure Molten Salt Co-Catalysis With Palladium on Alumina Versus No Co-Catalyst

| Run # | Co-Catalyst | Salt Temp. (°C.) | Feed Gas* | Conversions $C_3$ (%) | $O_2$ (%) | $CO_2$ | Hydrocarbons | Formaldehyde | Methanol | Acetaldehyde | Propylene oxide | Other |
|---|---|---|---|---|---|---|---|---|---|---|---|---|
| 1 | None | 350 | 1 | 0 | 0 | 0 | 0 | 0 | 0 | 0 | 0 | 0 |
| 2 | None | 350 | 2 | 0 | 0 | 0 | 0 | 0 | 0 | 0 | 0 | 0 |
| 3 | None | 400 | 1 | 20.9 | 89.5 | 35.0 | 5.8 | 4.6 | 2.2 | 17.2 | 17.8 | 17.3 |
| 4 | None | 400 | 2 | 12.5 | 100 | 31.0 | 10.2 | 3.1 | 0.6 | 18.7 | 18.5 | 17.5 |
| 5 | .3% Pd on alumina | 350 | 1 | 0 | 0 | 0 | 0 | 0 | 0 | 0 | 0 | 0 |
| 6 | .3% Pd on alumina | 350 | 2 | 0.2 | 1.9 | 21.9 | 1.3 | 12.4 | 0 | 22.1 | 27.9 | 14.4 |
| 7 | .3% Pd on alumina | 400 | 1 | 21.8 | 61.4 | 30.4 | 7.4 | 7.6 | 4.1 | 18.9 | 19.7 | 12.0 |
| 8 | .3% Pd on alumina | 400 | 2 | 13.4 | 100+ | 29.4 | 10.4 | 6.3 | 2.0 | 19.8 | 20.0 | 12.1 |

*1 25% $C_3H_6$/75% air; flow rate 1000 cc/minute
 2 88% $C_3H_6$/12% oxygen; flow rate 850 cc/minute The results as provided in TABLE I above indicated that palladium on alumina is an effective co-catalyst in conjunction with molten nitrate salt in enhancing the molar selectivity of propylene oxide production, as compared to the use of molten nitrate salt alone when carrying out the reaction with a propylene rich feed (Gas Composition 2). For example, at 350° C. Run 6 employing 0.3 weight percent palladium on alumina provided a propylene oxide selectivity of 27.9 percent, the highest seen at atmospheric pressure. In Run 2 wherein no palladium catalyst was employed there was no reaction. At 400° C. (compare Run 8 with Run 4 of TABLE I) a slight improvement (20.0 percent propylene oxide selectivity versus 18.5 percent propylene oxide selectivity) resulted.

Other potential co-catalysts, such as vanadium pentoxide on alumina, were found not to enhance propylene oxide selectivity at atmospheric pressure.

When a similar comparison was conducted under pressure of 75 psig, it was found that no co-catalyst was needed. Indeed under pressure, palladium on alumina provided decreased selectivity of propylene oxide.

EXAMPLE 3

Silver Nitrate as a Co-Catalyst

A salt mixture consisting of 1320 grams of sodium nitrate, 880 grams potassium nitrate, and 100 grams silver nitrate was added to a two-liter stainless steel autoclave with a Hastelloy C liner. The salt mixture was melted and brought up to 310° C. by means of an external electrical resistance heater. Propylene and air at the rate of 1000 cc/min were sparged into the melt through separate but concentric co-axial tubes with a sparging element attached to the end as in EXAMPLE 1. The experiment was conducted following the procedure of EXAMPLE 1 except that the salt temperature was held at 310° C. versus 350° C. EXAMPLE 1. Without a co-catalyst present, reaction does not normally occur at 75 psig at temperatures below 330° C. After a one hour run with the silver nitrate present, analysis of the reaction products showed that reaction did occur with a propylene conversion of 2 percent. The selectivity to propylene oxide was found to be 31 percent. The selectivity to the other products was found to be: acetaldehyde, 39 percent; carbon dioxide, 24 percent; and the remainder was found to be distributed between about six other compounds.

The results showed that the presence of silver nitrate accelerated the oxidation of propylene under the conditions employed such that the desired reaction occurred at a temperature 60° C. lower than normally seen.

EXAMPLE 4

Molybdenum Oxide (MoO₃) as a Co-Catalyst

A salt mixture consisting of 3700 grams sodium nitrate, 2500 grams potassium nitrate, and 50 grams molybdenum oxide, $MoO_3$, was charged to a four-liter autoclave reactor with a depth of approximately 68 cm and an internal diameter of 9 cm fitted with a Hastelloy C liner. The salt mixture was melted and brought up to 269° C. by means of an external electrical resistance heater. Propylene, 52 volume percent; oxygen, 5 volume percent; and nitrogen, 43 volume percent, were sparged into the melt as described in EXAMPLE 1 except at a pressure of 300 psig. The reaction was allowed to continue for one hour and the products were collected and analyzed as in EXAMPLE 1. The propylene conversion was found to be about 1 percent and the selectivity to propylene oxide was calculated to be 24 percent. The other product selectivities were found to be: acetaldehyde, 31 percent; carbon dioxide, 22 percent; formaldehyde, 4 percent; with the remainder being distributed among about 10 other products.

The use of molybdenum oxide as co-catalyst produced propylene conversions of about 1 percent at a temperature that was 50° C. below that normally seen for the pressure and feed gas composition employed.

What is claimed is:

1. A process for producing an alkylene oxide or mixture of alkylene oxides by a reaction which comprises reacting an olefin having from 3 to 22 carbon atoms per molecule, or mixture thereof, with an oxygen-containing gas, said olefin and said oxygen-containing gas being gaseous reactants, by contacting said gaseous reactants with a bath, stream, spray or mist of at least one molten nitrate salt catalyst and a co-catalyst, said catalyst being present in an amount sufficient to absorb any heat generated during said reaction while maintaining an essentially constant reaction temperature, said co-catalyst being an elemental metal, or oxide or hydroxide thereof, which is suspended, dispersed or dissolved in said catalyst, said reaction being conducted at a reaction temperature of between about 135° C. and about 600° C. and a reaction pressure of between about 1 and about 50 atmospheres.

2. The process of claim 1 wherein said co-catalyst is selected from the group consisting of elemental metals, and oxides and hydroxides thereof, and mixtures thereof.

3. The process of claim 1 wherein said co-catalyst is an alkali metal hydroxide.

4. The process of claim 3 wherein said alkali metal hydroxide is selected from the group consisting of sodium hydroxide, potassium hydroxide, and combinations thereof.

5. The process of claim 1 wherein said co-catalyst is palladium, silver, or molybdenum oxide.

6. The process of claim 1 wherein said molten nitrate salt is selected from the group consisting of sodium, potassium, lithium, cesium, magnesium, and calcium molten nitrate salts and mixtures thereof.

7. A method for producing an alkylene oxide from an olefin having from 3 to 22 carbon atoms per molecule or mixture thereof, which comprises bubbling gaseous reactants consisting of an oxygen-containing gas and said olefin, or mixture thereof, through a bath of at least one molten nitrate salt catalyst, in the presence of a co-catalyst, said catalyst being present in an amount sufficient to absorb any heat generated during said reaction while maintaining an essentially constant reaction temperature, said co-catalyst being an elemental metal, or oxide or hydroxide thereof, said reaction being conducted at a reaction temperature of between about 135° C. and about 600° C. and a reaction pressure of between about 1 and about 50 atmospheres.

8. The method of claim 7 wherein said oxygen-containing gas is fed into said bath by means of a first tube and wherein said olefin, or mixture thereof, is fed into said bath by means of a second tube.

9. The method of claim 8 wherein said first tube and said second tube are co-axially mounted with respect to each other.

10. The method of claim 7 wherein said olefin, or mixture thereof, has between 3 and 15 carbon atoms per molecule on average.

11. The process of claim 7 wherein said co-catalyst is palladium, silver, or molybdenum oxide.

12. The process of claim 7 wherein said co-catalyst is an alkali metal hydroxide.

13. The process of claim 12 wherein said co-catalyst is selected from the group consisting of sodium hydroxide, potassium hydroxide, and combinations thereof.

14. A process for producing an alkylene oxide or mixture of alkylene oxides by a reaction which comprises reacting an olefin having from 3 to 8 carbon atoms per molecule, or mixture thereof, with an oxygen-containing gas, said olefin and said oxygen-containing gas being gaseous reactants, by contacting said gaseous reactants with a bath, stream, spray or mist of at least one molten nitrate salt catalyst and a co-catalyst, said catalyst being present in an amount sufficient to absorb any heat generated during said reaction while maintaining an essentially constant reaction temperature, said co-catalyst being an elemental metal, or oxide or hydroxide thereof, which is suspended, dispersed or dissolved in said catalyst, said reaction being conducted at a reaction temperature of between about 135° C. and about 600° C. and a reaction pressure of between about 1 and about 50 atmospheres.

15. The process of claim 14 wherein said olefin has from 3 to 6 carbon atoms per molecule.

16. The process of claim 14 wherein said co-catalyst is selected from the group consisting of sodium hydroxide, potassium hydroxide, and combinations thereof.

17. The process of claim 14 wherein said co-catalyst is palladium, silver, or molybdenum oxide.

* * * * *